(12) United States Patent
Shastry et al.

(10) Patent No.: US 10,857,093 B2
(45) Date of Patent: Dec. 8, 2020

(54) MICROARRAY FOR DELIVERY OF THERAPEUTIC AGENT, METHODS OF USE, AND METHODS OF MAKING

(71) Applicant: Corium, Inc., Menlo Park, CA (US)

(72) Inventors: Ashutosh Shastry, Santa Clara, CA (US); Adrian Faasse, Carmel Valley, CA (US); Parminder Singh, Union City, CA (US)

(73) Assignee: Corium, Inc., Menlo Park, CA (US)

( * ) Notice: Subject to any disclaimer, the term of this patent is extended or adjusted under 35 U.S.C. 154(b) by 60 days.

(21) Appl. No.: 15/195,793

(22) Filed: Jun. 28, 2016

(65) Prior Publication Data
US 2016/0374939 A1    Dec. 29, 2016

Related U.S. Application Data

(60) Provisional application No. 62/186,310, filed on Jun. 29, 2015.

(51) Int. Cl.
*A61K 9/00* (2006.01)
*A61M 37/00* (2006.01)
(Continued)

(52) U.S. Cl.
CPC ....... *A61K 9/0021* (2013.01); *A61M 37/0015* (2013.01); *B29C 39/42* (2013.01); *A61M 2037/0046* (2013.01); *A61M 2037/0053* (2013.01); *A61M 2037/0061* (2013.01); *B29K 2105/0035* (2013.01);
(Continued)

(58) Field of Classification Search
CPC ............ A61K 9/0021; A61M 37/0015; A61M 2037/0061; A61M 2037/0046; A61M 2037/0053; B29C 39/42; B29K 2105/0035; B29K 2105/0064; B29K 2105/0073; B29L 2031/756
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Julinova et al., "Initiating Biodegradation of Polyvinylpyrrolidone in an Aqueous Aerobic Environment," Proceedings of ECOpole (2012).*
(Continued)

*Primary Examiner* — Christopher T Schatz
*Assistant Examiner* — Cynthia L Schaller
(74) *Attorney, Agent, or Firm* — McDermott, Will & Emery LLP; Judy M. Mohr; Edward J. DesJardins

(57) ABSTRACT

Devices and methods for manufacturing and using microstructure arrays are described. In the methods, formulation is introduced into cavities of a microprojection array mold by means that include a vacuum to achieve a more efficient and uniform filling of the cavities and/or reduce bubble formation in the cavities.

23 Claims, 3 Drawing Sheets

(51) Int. Cl.
  *B29C 39/42* (2006.01)
  *B29K 105/00* (2006.01)
  *B29L 31/00* (2006.01)
(52) U.S. Cl.
  CPC .............. *B29K 2105/0064* (2013.01); *B29K 2105/0073* (2013.01); *B29L 2031/756* (2013.01)

(56) References Cited

U.S. PATENT DOCUMENTS

| | | |
|---|---|---|
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier et al. |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusack et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabenau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrecich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |

(56) References Cited

U.S. PATENT DOCUMENTS

| | | |
|---|---|---|
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Gartstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whitson |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 | 5/2006 | Frazier et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Aderhold et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Ghartey-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 | 1/2017 | Woolfsen et al. |
| 9,687,640 B2 | 6/2017 | Trautman et al. |
| 9,687,641 B2 | 6/2017 | Singh et al. |
| 9,962,534 B2 | 5/2018 | Chen et al. |
| 10,195,409 B2 | 2/2019 | Bourne et al. |
| 10,238,848 B2 | 3/2019 | Singh et al. |
| 10,245,422 B2 | 4/2019 | Le et al. |
| 10,384,045 B2 | 8/2019 | Ding et al. |
| 10,384,046 B2 | 8/2019 | Bayramov et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |

(56) References Cited

U.S. PATENT DOCUMENTS

| | | |
|---|---|---|
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 | 3/2004 | Mazess et al. |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinaga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0224377 A1* | 9/2007 | Leimbacher ............ C08L 67/02 428/36.92 |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0063866 A1 | 3/2008 | Allen et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Frederickson et al. |
| 2008/0200883 A1 | 8/2008 | Tomono |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0262444 A1 | 10/2008 | Takada |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2009/0234301 A1* | 9/2009 | Tomono ............ A61M 37/0015 604/272 |
| 2010/0004608 A1 | 1/2010 | Hamamoto et al. |
| 2010/0028390 A1 | 2/2010 | Cleary et al. |
| 2010/0200494 A1 | 8/2010 | Storer |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0165236 A1 | 7/2011 | Chow et al. |
| 2011/0177139 A1 | 7/2011 | Jung et al. |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1 | 12/2011 | Kaufmann et al. |
| 2011/0306853 A1 | 12/2011 | Black et al. |
| 2012/0052120 A1 | 3/2012 | Castor |
| 2012/0123297 A1 | 5/2012 | Brancazio |
| 2012/0123387 A1 | 5/2012 | Gonzalez et al. |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0150822 A1 | 6/2013 | Ross |
| 2013/0156849 A1 | 6/2013 | De Fougerolles et al. |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2014/0330198 A1 | 11/2014 | Zhang et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0015952 A1 | 1/2016 | Omachi et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0050010 A1* | 2/2017 | Mcallister ......... A61M 37/0015 |
| 2017/0217656 A1* | 8/2017 | Yamada ............ A61M 37/0015 |
| 2017/0281535 A1 | 10/2017 | Singh et al. |
| 2017/0361079 A1 | 12/2017 | Trautman et al. |
| 2019/0001109 A1 | 1/2019 | Kim et al. |
| 2019/0184147 A1 | 6/2019 | Singh et al. |
| 2019/0184148 A1 | 6/2019 | Le et al. |
| 2019/0336741 A1 | 11/2019 | Bayramov et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |

(56) References Cited

FOREIGN PATENT DOCUMENTS

| | | |
|---|---|---|
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 1377338 B1 | 6/2008 |
| EP | 2283809 A1 | 2/2011 |
| EP | 2399624 A1 | 12/2011 |
| FR | 2535602 | 5/1984 |
| GB | 0788479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2008-534881 A | 11/2003 |
| JP | 2004-065775 A | 3/2004 |
| JP | 2006/271781 A | 10/2006 |
| JP | 2006-341089 A | 12/2006 |
| JP | 2007-130030 A | 5/2007 |
| JP | 2007-190112 A | 8/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1996/038174 A1 | 12/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030281 A1 | 4/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000388 A2 | 12/2003 |
| WO | WO 2004/009172 A1 | 1/2004 |
| WO | WO 2004/020034 A2 | 3/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/044333 A2 | 5/2005 |
| WO | WO 2005/046769 A2 | 5/2005 |
| WO | WO 2005/065765 A1 | 7/2005 |
| WO | WO 2005/067889 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |

(56) References Cited

FOREIGN PATENT DOCUMENTS

| | | |
|---|---|---|
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/093679 A1 | 8/2008 |
| WO | WO 2008/130587 | 10/2008 |
| WO | WO 2008/139648 A1 | 11/2008 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/101639 A2 | 8/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2016/149152 A2 | 9/2016 |
| WO | WO 2017/004067 A1 | 1/2017 |
| WO | WO 2017/116076 A1 | 7/2017 |

OTHER PUBLICATIONS

"Material Safety Data Sheet Polysorbate 80 MSDS" (2005) from ScienceLab.com.*
International Search Report from International Patent Application No. PCT/US2016/039864 dated Sep. 23, 2016.
Lutrol F 68 NF, BASF Pharma Ingredients, accessed from the internet on Sep. 5, 2016 from http://www2.basf.us/Pharma/pdf/Lutrol_F_68.pdf.
Makaida et al., "Poly lactic-co-glycolic acid (PLGA) as biodegradable controlled drug delivery carrier", Polymers (Basel), vol. 3, No. 3, pp. 1377-1397 (2011).
International Search Report from International Patent Application No. PCT/US2011/035221 dated Jan. 10, 2012, application now published as International Publication No. WO2011/140240 on Nov. 10, 2011.
Avcin et al., "Subcutaneous nodule after vaccination with an aluminum-containing vaccina", Acta Dermatoven, APA, vol. 17, No. 4, pp. 182-184 (2008).
Chun, et al., "An array of hollow microcapillaries for the controlled injection of genetic materials into animal/plant cells," IEEE Workshop on Micro Electro Mechanical Systems, pp. 406-411, (1999).
Corbett et al., "Skin vaccination against cervical cancer associated human papillomavirus with a novel micro-projection array in a mouse model", PLOS one, vol. 5, No. 10, pp. 1-9 (2010).
Database WPI / Thomson, Accession No. 2014-V89218, Gao et al., "Soluble microneedle patch useful for transdermal administration of vaccine, comprises water-soluble polymer materials as matrix material and soluble microneedle main portion", Application No. CN10427324A, Tech Inst Phys. & Chem. Chinese Acad., 3 pages (2014).
"Eudragit EPO Readymix—Taste masking and moisture protection have ever been easier" Evonik Industries, Evonik Industries AG, Pharam Polymers & Services, Nov. 2014.
"Extended", Meriam-Webster Online Dictionary, 6 pages, Downloaded on Sep. 7, 2010 from <http://www.merriam-webster.com/dictionary/extend>.
"Extended", Macmilliam Online Dictionary, 5 pages, Downloaded on Sep. 7, 2010 from <http://www.macmillandictinoary.com/dictionary/american/extended>.
Ghost et al., "Influence of critical parameters of nanosuspension formulation on permeability of a poorly solube drug through the skin-A case study", vol. 14, No. 3, pp. 1108-1117 (2013).
Guo et al., "Enchanced transcutaneous immunization via dissolving microneedle array loaded with liposome encapsutated antigen and adjuvant", Int. J. Pharm., vol. 447, No. 1-2, pp. 22-30 (2013).
Gupta, "Aluminum compounds as vaccine adjuvants", Adv. Drug Deliv. Rev., vol. 32, No. 3, pp. 155-172 (1998) Abstract Only.
Gupta and Rost, "Aluminum compounds as vaccine adjuvants", Vaccine adjuvants: Preparation Methods and Research Protocols, O'Hagan. ed., Humana Press, Inc., Totowa, New Jersey, Meth. Mol. Med., vol. 42, No. 4, No, 4, pp. 65-89 (2000).
Henry, et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from International Patent Application No. PCT/US2000/015612 dated Sep. 7, 2000.
International Search Report from International Patent Application No. PCT/US2000/015613 dated Sep. 6, 2000.
International Search Report from International Patent Application No. PCT/US2000/015614 dated Sep. 6, 2000.
International Search Report from International Patent Application No. PCT/US2001/031977 dated Apr. 28, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017255 dated May 24, 2005.
International Search Report from International Patent Application No. PCT/US2005/009854 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 Oct. 30, 2008.
International Search Report from International Patent Application No. PCT/US2008/011635 dated Dec. 19, 2008, application now published as International Publication No. WO2009/048607 on Apr. 16, 2009.
International Search Report from International Patent Application No. PCT/US2010/032299 dated Dec. 10, 2010, application now published as International Publication No. WO2010/124255 on Oct. 28, 2010.
International Search Report from International Patent Application No. PCT/US2013/077281 dated Mar. 4, 2013.
International Search Report from International Patent Application No. PCT/US2014/021841 dated Aug. 11, 2014.

(56) References Cited

OTHER PUBLICATIONS

International Search Report from International Patent Application No. PCT/US2014/022087 dated May 23, 2014.
International Search Report from International Patent Application No. PCT/US2014/022836 dated May 9, 2015.
International Search Report from International Patent Application No. PCT/US2014/022859 dated May 26, 2014.
International Search Report from International Patent Application No. PCT/US2014/026179 dated Jul. 18, 2014.
International Search Report from International Patent Application No. PCT/US2014/029601 dated Jul. 1, 2014.
International Search Report from International Patent Application No. PCT/US2015/047563 dated Nov. 20, 2015.
International Search Report from International Patent Application No. PCT/US2015/048161 dated Nov. 26, 2015.
International Search Report from International Patent Application No. PCT/US2015/059559 dated Jan. 21, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Kuroda et al., "Particulate adjuvant and innate immunity: past achievements, present findings, and future prospects", Int. Rev. Immunol., vol. 32, No. 2, pp. 209-220 (2013).
Matriano, et al., "Macroflux(R) microprojection array patch technology: A new and efficient approach for intracutaneous immunization", Pharm. Res., vol. 19, No. 1, pp. 63-70, (2002).
McAllister, et al., "Micromachined microneedles for transermal drug delivery", Am. Inst. Chem. Eng., 1998 Annual Meeting, Miami Beach, FL, Nov. 15-20, Drug Delivery II, pp. 1-4.
Mikszta, et al., "Improved genetic immunication via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inl. Dis., vol. 191, No. 2, pp. 278-288, (2005).
Munks et al., "Aluminum adjuvant elicit fibrin-dependent exracellular traps in vivo", Blood, vol. 116, No. 24, pp. 5191-5199 (2010).
Papautsky, et al., "Micromachined Pipette Arrays," MPA, Proceedings—19th international Conference—IEEE/EMBS, Chicago IL, USA, pp. 2281-2284 (1997).
Park et al., "Biodegradable polymer microneedles: Fabrication, mechanics, and transdermal drug delivery", J. Contr. Rel., vol. 104, pp. 51-66 (2005).
Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).
Petrovsky and Aguilar, "Vaccine adjuvants: current state and future trends", Immunol. Cell Biol., vol. 82, No. 5, pp. 488-496 (2004).
Pittman, "Aluminum-containing vaccine associated adverse events: role of route of administration and gender", Vaccine, vol. 20, pp. s48-s50 (2002).
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).
Prausnitz, "Microneedle-based vaccines", Curr. Top. Microbiol. Immunol., vol. 333, pp. 369-393 (2009).
Rydberg, et al., "Low-molecular-weight heparin preventing and treating DVT", Am. Fam. Physician, vol. 59, No. 6, pp. 1607-1612, (1999).
Sayers et al., "Vaxjo: A Web-Based Vaccine Adjuvant Database and Its Applications for Analysis of Vaccine Adjuvants and Their Uses in Vaccines Development", J. Biomed. Biotechnol., vol. 2012, Article ID: 831486, 13 pages, doi:10.1155/2012/831486 (2011).
Sivamani, et al., "Microneedles and transdermal applications", Exp. Opin. Drug Del., vol. 4, No. 1, pp. 19-25, (2007).
Vitiello et al., "Development of a lipopetide-based therapeutic vaccine to trent chronic HBV infection", J. Clin, Invest., vol. 95, pp. 341-349 (1995).
White et al., "Studies on antibody production. III. The alum granuloma", J. Exp. Med., vol. 102, No. 1, pp. 73-82 (1955).
Wouters et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).
Kunduru et al., "Biodegradable polymers: Medical Applications", Encyclopedia of Polymer Science and Technology, pp. 1-22 (2016) DOI: 10.1002/0471440264.pst027.pub2.
International Search Report from International Patent Application No. PCT/US2019/039028 dated Sep. 13, 2019.

\* cited by examiner

MICROARRAY FOR DELIVERY OF THERAPEUTIC AGENT, METHODS OF USE, AND METHODS OF MAKING

CROSS-REFERENCE TO RELATED APPLICATIONS

This application claims the benefit of U.S. Provisional Application No. 62/186,310, filed Jun. 29, 2015, which is incorporated herein by reference in its entirety.

TECHNICAL FIELD

The disclosure relates generally to methods for making or fabricating the delivery systems for administering a therapeutic agent or drug using an array of microstructures, methods for using the systems for delivery of an agent, and related features thereof.

BACKGROUND

Arrays of microneedles were proposed as a way of administering drugs through the skin in the 1970s, for example in expired U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A further description of the fabrication of a microneedle array made of polyglycolic acid is found in Park et al, "Biodegradable polymer microneedles: Fabrication, mechanics, and transdermal drug delivery," *J. of Controlled Release*, 104:51-66 (2005).

A method of forming microprotrusion arrays using solvent casting methods is described in U.S. Publication Nos. 2008/0269685 and 2014/0272101, which are incorporated in their entirety herein by reference.

A layered microstructure array has been described in U.S. Publication No. 2011/0276028, incorporated in its entirety herein, for hPTH delivery comprising a fast dissolving drug-in-tip distal layer and a backing layer formed of an insoluble biodegradable polymer.

Despite these efforts, there is still a need to find simpler and better methods for the manufacture of polymeric delivery systems. A particular need is for systems and methods that provide better, more consistent and easier formation of the arrays as well as providing methods that are useful for commercial manufacture of arrays. A further need is for a method of forming microstructure arrays that is scalable from small scale, aseptic and pilot testing to commercial processes.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method of making or preparing an array of microstructures. In some embodiments, the method comprises dissolving or suspending at least one therapeutic or active agent in a first solvent to form a therapeutic or active agent solution or suspension. At least one polymer is dissolved in a second solvent, which may be the same or different than the first solvent, to form a polymer matrix solution or suspension. In some embodiments, at least one of the first or second solvent is water or an aqueous solution. The therapeutic or active agent solution or suspension and the polymer solution are mixed to form a polymer matrix solution or suspension.

In some embodiments, the therapeutic or active agent solution or suspension and/or the polymer solution or suspension includes one or more excipients and/or additives. In some embodiments, the excipient or additive is selected from one or more of a sugar, a surfactant, or an antioxidant. In some embodiments, one or more of the excipients or additives is dissolved in at least one of the first or second solvent. In some embodiments, the sugar is selected from sorbitol, sucrose, trehalose, fructose, or dextrose. In some embodiments, the surfactant is selected from Polysorbate 20 or Polysorbate 80. In some embodiments, the antioxidant is selected from methionine, cysteine, D-alpha tocopherol acetate, EDTA, or vitamin E. Where the excipient is a sugar, in some embodiments the at least one sugar is dissolved in the polymer matrix or suspension after the polymer is dissolved in the solvent.

In embodiments, the therapeutic or active agent is selected from one or more of a drug, a small molecule, a peptide or a protein, and/or a vaccine.

A low vacuum is applied to a mold having a plurality of microstructure cavities formed therein. The polymer matrix solution or suspension is dispensed on the mold and the microstructure cavities in the mold are filled with the polymer matrix solution or suspension. The solution or suspension is dried to form the array of microstructures. In embodiments, the low vacuum is applied to achieve a vacuum pressure of about $1 \times 10^{-3}$ to 760 Torr. In other embodiments, the low vacuum is applied to achieve a vacuum pressure of about 25 to 760 Torr. In some embodiments, the dispensing and/or filling steps are performed outside the low vacuum. In some embodiments, excess polymer matrix solution or suspension is removed from the mold, including the mold surface, after the filling step.

In some embodiments, the method further comprises dispensing at least one soluble gas into the cavities prior to applying the low vacuum to the mold. In some embodiments, the method further comprises dispensing at least one soluble gas into the cavities prior to dispensing the polymer matrix solution or suspension on the mold. In some embodiments, the soluble gas is selected from $CO_2$ and $CH_4$.

In some embodiments, the polymer matrix solution or suspension is dried at a temperature of about 5-50° C. In some embodiments, the polymer matrix solution or suspension is dried for at least about 30-60 minutes.

In some embodiments, the method further comprises dispensing a basement or backing layer formulation on the mold surface. In embodiments, the basement or backing layer formulation is dispensed such that the basement or backing layer formulation contacts the polymer matrix to connect the dried microstructure (polymer matrix) portions. In some embodiments, the basement or backing layer formulation is dried in an oven at about 5-50° C. In some embodiments, the basement or backing layer is comprised of at least one non-biodegradable polymer.

In some embodiments, the basement or backing layer is affixed to a substrate. In some embodiments, the substrate is selected from a pressure sensitive adhesive and a UV cured adhesive.

In some embodiments, the method further comprises demolding the array from the mold. In some embodiments, the array is demolded from the mold drying the basement or backing layer.

Additional embodiments of the present microstructures, arrays, methods, apparatuses, devices, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

Figure 1:
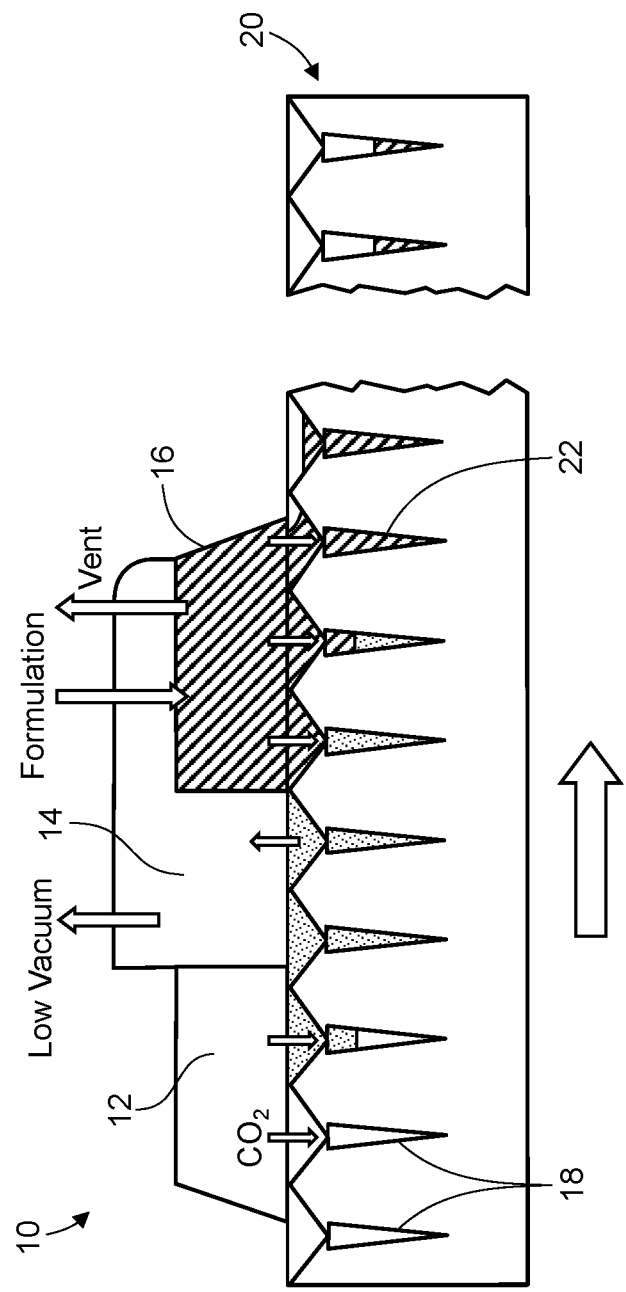
FIG. 1 is an illustration of one embodiment of a method of casting microprojections.

It will be appreciated that the thicknesses and shapes for the various microstructures have been exaggerated in the drawings to facilitate understanding of the device. The drawings are not necessarily "to scale."

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

The terms "microprotrusion", "microprojection", "microstructure" and "microneedle" are used interchangeably herein to refer to elements adapted to penetrate or pierce at least a portion of the stratum corneum or other biological membrane. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

In discussing the applicators and arrays described herein, the term "downward" is sometimes used to describe the direction in which microprotrusions are pressed into skin, and "upward" used to describe the opposite direction. However, those of skill in the art will understand that the applicators can be used where the microprotrusions are pressed into skin at an angle to the direction of the earth's gravity, or even in a direction contrary to that of the earth's gravity. In many applicators, the energy for pressing the microprotrusions is provided primarily by an energy-storage member and so efficiency is not much affected by the orientation of the skin relative to the earth's gravity.

In this application reference is often made for convenience to "skin" as the biological membrane which the microprojections penetrate. It will be understood by persons of skill in the art that in most or all instances the same inventive principles apply to the use of microprojections to penetrate other biological membranes such as, for example, those which line the interior of the mouth or biological membranes which are exposed during surgery.

"Biodegradable" refers to natural or synthetic materials that degrade enzymatically, non-enzymatically or both to produce biocompatible and/or toxicologically safe by-products which may be eliminated by normal metabolic pathways.

"Medium vacuum" refers to a partial pressure that may be achieved with a vacuum pump. A medium pressure may not be measurable using a liquid or mechanical manometer. In embodiments, a medium vacuum refers to a pressure of about 25 to $1 \times 10^{-3}$ Torr.

The term "microprotrusion array" for purposes herein is intended to denote a two-dimensional or a three-dimensional arrangement of microprotrusions, microstructures, microprojections, or microneedles, which are used interchangeably herein. The arrangement may be regular according to a repeating geometric pattern or it may be irregular. A typical "microstructure array", "microprojection array", or "microneedle array" comprises microstructures, microprojections, or microneedles projecting from a base or substrate of a particular thickness, which may be of any shape, for example square, rectangular, triangular, oval, circular, or irregular. An array typically comprises a plurality of microstructures, microprojections, or microneedles. The microstructures, microprojections, or microneedles themselves may have a variety of shapes. While an array could be pressed by hand into skin, a variety of devices may be used to hold the array as it is being applied and/or to facilitate in one way or another the process of application of the array to the skin or other biological membrane. Such devices may broadly be referred to as "applicators." Applicators may for example reduce the variations in force, velocity, and skin tension that occur when an array is pressed by hand into the skin. Variations in force, velocity and skin tension can result in variations in permeability enhancement.

"Non-biodegradable" refers to natural or synthetic materials that do not appreciably degrade when inserted into and/or contacted with skin, mucosa, or other biological membrane for a period of time associated with use of microstructure arrays.

"Optional" or "optionally" means that the subsequently described circumstance may or may not occur, so that the description includes instances where the circumstance occurs and instances where it does not.

"Rough vacuum" or "low vacuum" refers to a partial pressure of less than 1 atmosphere (760 Torr). In embodiments, a rough or low vacuum refers to a pressure of about 760 to 25 Torr.

"Substantially" or "essentially" means nearly totally or completely, for instance, 90-95% or greater of some given quantity.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed, as well as the range of values greater than or equal to 1 µm and the range of values less than or equal to 8 µm.

I. METHODS OF MAKING MICROSTRUCTURE ARRAYS

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

Examples of forming various microstructure arrays using different formulations and configurations are provided in Example 1.

A. Array Molds

The molds used to form the arrays in the methods herein can be made using a variety of methods and materials. Exemplary molds and methods of making molds are described, for example, in U.S. Patent Publication No. 2008/2696585. In one exemplary embodiment, the mold is a negative mold formed from a silicone such as polydimethylsilicone. A negative mold is typically formed by preparing a master microprojection array and casting a liquid mold material over the master array. The mold is allowed to dry and harden, which results in a mold comprising cavities corresponding to the microprojections of the master array. It will be appreciated that the molds suitable for use in the present methods may be prepared according to other methods.

In general, the microprojections have a height of at least about 100 µm, at least about 150 µm, at least about 200 µm, at least about 250 µm, or at least about 300 µm. In general it is also preferred that the microprojections have a height of no more than about 1 mm, no more than about 500 µm, no more than about 300 µm, or in some cases no more than about 200 µm or 150 µm. In embodiments, the microprojections have a height of at least about 50-500 µm. In other embodiments, the microprojections have a height of at least about 100-500 µm, 100-400 µm, 100-300 µm, 100-200 µm, 100-150 µm, 150-500 µm, 150-400 µm, 150-300 µm, 150-200 µm, 200-500 µm, 200-400 µm, 200-300 µm, 300-500 µm, 300-400 µm, or 400-500 µm. It will be appreciated that the microprojections within an array may have a range of heights. The microprojections may have any suitable shape including, but not limited to polygonal or cylindrical. Particular embodiments include pyramidal including a four-sided pyramid, a funnel shape, a cylinder, a combination of funnel and cylinder shape having a funnel tip and a cylindrical base, and a cone with a polygonal bottom, for example hexagonal or rhombus-shaped. Other possible microprojection shapes are shown, for example, in U.S. Published Patent Apps. 2004/0087992 and 2014/0180201. Microprojections may in some cases have a shape which becomes thicker towards the base, for example microprojections which have roughly the appearance of a funnel, or more generally where the diameter of the microprojection grows faster than linearly with distance to the microprojection distal end. It will be appreciate that polygonal microprojections may also have a shape which becomes thicker toward the base or where a radius or diameter grows faster than linearly with distance to the microprojection distal end. Where microprojections are thicker towards the base, a portion of the microprojection adjacent to the base, which may be called the "foundation," may be designed not to penetrate the skin.

The microprojections may be spaced about 0-500 µm apart. In specific, but not limiting embodiments, the microprojections are spaced about 0 µm, about 50 µm, about 100 µm, about 150 µm, about 200 µm, about 250 µm, about 300 µm, about 350 µm, about 400 µm, about 450 µm, or about 500 µm apart. The space between the microprojections may be measured from the base of the microprojections (base to base) or from the tip (tip to tip). The spacing of the microprojections may be regular or irregular.

One exemplary master array includes a plurality of diamond shaped projections having a height of about 200 µm, a base of about 70 μm, and spacing between the projections of about 200 μm. In another exemplary embodiment, the master array includes a plurality of hexagonal or other polygonal shaped projections having a height of about 200 μm, a base of about 70 μm, and spacing between the projections of about 400 μm. In yet another embodiment, the master array includes a plurality of cylindrical shaped projections having a height of about 400 μm, a diameter of about 100 μm, and spacing between the projections of about 200 μm. It will be appreciated that the cylindrical shaped projections may have a funnel shaped, pointed, or sharp distal end.

B. Preparation of Casting Solution or Formulation

For the active agent containing portion of the microstructures, a casting solution or formulation is formed by dissolving or suspending one or more therapeutic agents, active agents, drugs, APIs, or other substances to be transdermally delivered and one or more polymers in a solvent to form a polymer matrix solution or suspension. The terms active agent, therapeutic agent, agent, drug, API are used interchangeably herein and discussion or reference to one is intended to include and apply to each and all terms. In one embodiment, the casting solution is formed by dissolving or suspending at least one agent and one or more polymers in an aqueous buffer or solvent to form a solution or suspension comprising the active agent and the polymer. In another embodiment, at least one active agent is dissolved or suspended in a solvent to form an active agent solution or suspension. At least one polymer is separately dissolved in a solvent to form a polymer solution or suspension. The suspension may be a liquid in liquid suspension or a solid in liquid suspension depending on the nature of the active agent and/or polymer. The solvent used for the active agent solution and the polymer solution may be the same or different. The active agent solution and the polymer solution are mixed to form a polymer matrix solution or suspension. It will further be appreciated that a solvent mixture may be used to dissolve or suspend the active agent and/or polymer.

Casting solvents are preferably aqueous solvents. Suitable aqueous solvents include, but are not limited to, water, alcohols (for example, $C_1$ to $C_8$ alcohols such as propanol and butanol), alcohol esters, or mixtures of thereof. In other embodiments, the solvents are non-aqueous. Suitable non-aqueous solvents include, but are not limited to, esters, ethers, ketones, nitrites, lactones, amides, hydrocarbons and their derivatives as well as mixtures thereof. In other non-limiting embodiments, the solvent is selected from acetonitrile (ACN), dimethyl sulfoxide (DMSO), water, or ethanol. It will be appreciated that the choice of solvent may be determined by one or more properties of the active agent and/or polymer. It will further be appreciated that the casting solvent may comprise a mixture of solvents.

Any suitable drug, therapeutic agent, API, or other active agent may be dissolved or suspended in the solvent. The present arrays are suitable for a wide variety of substances or agents. Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In embodiments, the active agent is a biological agent including, but not limited to peptides, polypeptides, proteins, or nucleic acids (e.g. DNA or RNA). In one embodiment, the active agent is a polypeptide such as human parathyroid hormone (e.g. hPTH(1-34)), a protein such as human growth hormone, or an antibody. Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. In an embodiment, the vaccine comprises an antigen epitope conjugated on or to a carrier protein. It will be appreciated that vaccines may be formulated with our without an adjuvant. Suitable vaccines include, but are not limited to, vaccines for use against anthrax, diphtheria/tetanus/pertussis, hepatitis A, hepatitis B, *Haemophilus influenzae* type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

Additional agents include those directed against avian (pandemic) influenza virus, *Campylobacter* sp., *Chlamydia* sp., *Clostridium botulinum, Clostridium difficile*, dengue fever virus, *E. coli*, Ebola virus, Epstein Barr virus, non-typeable *Haemophilus influenzae*, hepatitis C, hepatitis E, herpes viruses including herpes zoster, HIV, leishmanial and malarial parasites, meningococcal serogroup B, nicotine, parainfluenza, ragweed allergen, respiratory syncytial virus (RSV), Rift Valley fever virus, SARS-associated coronavirus, *Shigella* sp., *Staphylococcus aureus, Streptococcus* Group A (GAS), *Streptococcus* Group B (GBS), tick-borne encephalitis, Venezuelan equine encephalitis, and West Nile virus.

It will be appreciated agents include those typically used for veterinary uses including vaccines for cats, dogs and other small animals as well as those for use with livestock such as cattle, pigs, goats, horses, chickens, etc. Veterinary agents include those directed against parvovirus, distemper virus, adenovirus, parainfluenza virus, *Bortadella bronchiseptica, Leptospira* spp., *Borrelia burgdorferi*, feline herpesvirus, feline calcivirus, feline panleukopenia virus, feline leukemia virus, feline immunodeficiency virus, and *Chlamydia felis*. Veterinary agents further include those directed against viral respiratory diseases (infectious bovine rhinotracheitis—IBR, bovine viral diarrhea—BVD parainfluenza-3 virus—Pl3, bovine respiratory syncytial virus—BRSV), *Campylobacter fetus* (Vibriosis) *Leptospirosis* sp., *Trichomoniasis, Moraxella bovis* (pinkeye), Clostridial (Blackleg), Brucellosis, *Mannheimia haemolytica, Pasteurella multocida, Haemophilus somni, Escherichia coli*, Anaplasmosis, foot-and-mouth disease virus (FMDV), procine parvovirus, swine fever, porcine reproductive and respiratory syndrome virus (PRRS), swine influenza, transmissible gastro enteritis virus (TGE), *Staphylococcus hyicus, Actinobacillus pleuropneumonia*, Atrophic rhinitis, Enzootic pneumonia, *Haemophilus parasuis, Streptococcal meningitis, Mycoplasma gaffisepticum*, Salmonella, Marek's Disease virus, and infectious bronchitis virus. Further veterinary agents include those directed against Eastern/Western Equine Encephalomyelitis, Equine influenza, Potomac Horse Fever, Strangles, Equine Herpesvirus, and Equine Viral Arteritis.

It will be appreciated that the vaccines described herein may include one or more antigens and one or more adjuvants. For example, the seasonal flu vaccine typically includes agents directed against several strains of influenza. Where multiple antigens are included in the vaccine, the antigens may be directed to conferring an immune response to one or more bacteria, virus, or microorganism. For example, more than one antigen specific to the same bacteria, virus or microorganism may be included in the vaccine. Alternatively, multiple antigens specific to different bacteria, viruses, or microorganisms may be included in the vaccine. Where the vaccine includes multiple antigens, the vaccine may include multiple adjuvants. The number of adjuvants included in the vaccine may be the same, less or more than the number of corresponding antigens included in the vaccine. In an embodiment, a vaccine including a single antigen may include multiple adjuvants.

In another embodiment, at least a portion of the distal layer comprises an agent suitable for veterinary uses. Such uses include, but are not limited to, therapeutic and diagnostic veterinary uses.

Polymers for use in the methods are typically biocompatible. In one embodiment, at least some of the polymers are biodegradable.

In an embodiment, the polymer is a structure-forming polymer. In an embodiment, the polymer is a hydrophilic water soluble polymer. Suitable polymers are known in the art and described, for example, in U.S. Patent Application No. 2008/0269685. Exemplary biocompatible, biodegradable, or bioerodible polymers include poly(lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteram ides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), block copolymers of polyethylene glycol-poly(lactic acid-co-glycolic acid) (PLGA-PEG), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), polysaccharides, polyalcohols, gelatin, alginate, chitosan, hyaluronic acid and its derivatives, collagen and its derivatives, polyurethanes, and copolymers and blends of these polymers. One hydroxyethyl starch may have a degree of substitution of in the range of 0-0.9. An exemplary polysaccharide is dextran including dextran 70, dextran 40, and dextran 10.

The casting solution may further include one or more excipients dissolved or suspended in the buffer or solvent. Suitable excipients include, but are not limited to, one or more stabilizers, plasticizers, surfactants, and/or anti-oxidants.

In one embodiment one or more sugars is added to the casting solution. Sugars can stabilize the active ingredient and/or plasticize at least one of the polymers. Sugars may also be used to affect, moderate, or regulate degradation of the polymer(s). Exemplary sugars include, but are not limited to, dextrose, fructose, galactose, maltose, maltulose, iso-maltulose, mannose, lactose, lactulose, sucrose, and trehalose, and sorbitol. In other embodiments, a sugar alcohol as known in the art is included in the casting solution. Exemplary sugar alcohols include, but are not limited to, lactitol, maltitol, sorbitol, and mannitol. Cyclodextrins can also be used advantageously in microprojection arrays, for example α, β, and γ cyclodextrins. Exemplary cyclodextrins include hydroxypropyl-β-cyclodextrin and methyl-β-cyclodextrin. In other embodiments, where Dextran, hetastarch and/or tetrastarch is used as a polymer in the casting solution, sorbitol may preferably be included in the casting solution. In this embodiment, sorbitol may not only stabilize the active agent, but also plasticize the polymer matrix, which reduces brittleness. The biodegradability or dissolvability of the microprojection array may be facilitated by the inclusion of sugars. Sugars and sugar alcohols may also be helpful in stabilization of peptides, proteins, or other biological active agents and in modifying the mechanical properties of the microprojections by exhibiting a plasticizing-like effect. Where the active agent is a biological agent including, but not limited to, peptides, proteins, and antibodies, one or more sugars or sugar alcohols may be used in the casting solution as a stabilizing agent. The sugar may be added to (i) the therapeutic agent solution or suspension, (ii) the polymer solution or suspension, or (iii) the polymer matrix solution or suspension once (i) and (ii) have been mixed.

One or more surfactants may be added to the casting solution to change the solutions' surface tension and/or reduce the hydrophobic interactions of proteins. Any suitable surfactant as known in the art may be used. Exemplary surfactants include, but are not limited to, emulsifiers such as Polysorbate 20 and Polysorbate 80.

One or more antioxidants may be added to the casting solution. Any suitable antioxidant as known in the art may be used. Exemplary antioxidants include, but are not limited to, methionine, cysteine, D-alpha tocopherol acetate, EDTA, and vitamin E.

C. Formation of Microstructure Arrays

Figure 2:
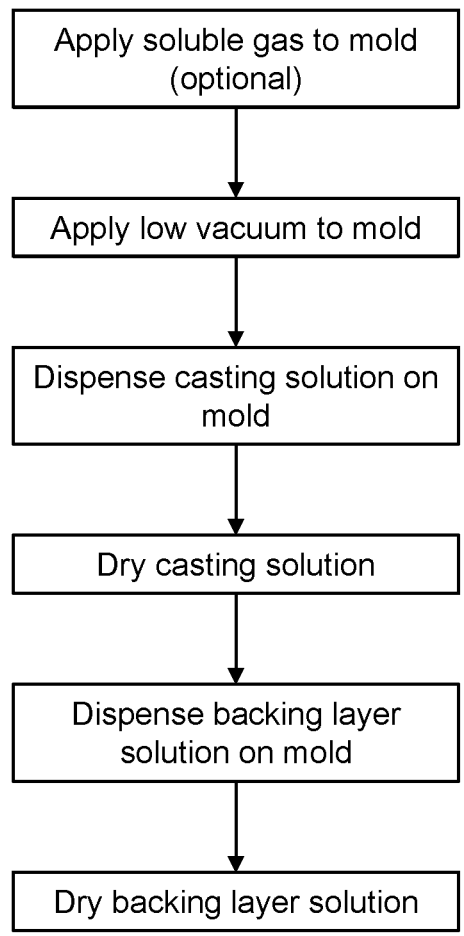
FIG. 2 is a flowchart of one method of forming a microprojection array.

In a general method, a casting solution is dispensed onto the mold or into the mold cavities. The casting solution is moved into the cavities. The casting solution is dried to form a solid polymer. Optionally, a backing or basement layer is cast on the mold and dried. A further optional substrate layer is applied to the backing or basement layer. A flow chart of an exemplary method of forming a microstructure array is shown in FIG. 2.

Filling the cavities of the mold with the liquid formulations has been a challenge. In casting a solution on the mold, it is commonly desired to avoid the presence of bubbles of air between the casting solution and the mold during casting. Due to the shape required to produce a sharp tip and/or the surface properties of the mold, bubbles often form/are trapped between the formulation and the mold surface as the liquid casting solution is moved into the mold cavities. This may be more prevalent at the deepest portion of the mold cavities. Air bubbles may be trapped especially at the tip of the cavities. If the formulation does not fill the cavities, the resulting microstructures may not have the desired shape including gaps and/or not have the required sharp tip. The shape of the meniscus for the casting solution in the cavity and/or the extent of filling the cavity is dependent upon the contact angle behavior of the casting solution on the mold surface.

Various approaches have been used to minimize or remove air bubbles in the cavities. The mold may be treated prior to dispensing the casting solution to improve dispensing of the casting solution and/or to avoid or reduce the presence of air bubbles. The mold itself, or portions of it, may be subject to surface treatments which make it easier for the solution to wet the mold surface. Suitable treatments are known in the art and described, for example, in U.S. Patent Publication No. 2008/0269685, which is incorporated herein in its entirety. U.S. Patent Publication No. 2008/0269685 describes applying a vacuum over the cavities while the casting solution is dispensed into the mold cavities. When the vacuum is removed, the higher pressure over the liquid film will shrink the bubble in the cavity and push the casting solution into the cavity.

A further approach is described, for example, in U.S. Patent Publication No. 2014/0272101, which is incorporated herein in its entirety, where the mold with the casting solution is pressurized to move the solution into the cavities. The pressurization shrinks the size of the air bubble as expected by Boyle's Law. For example, an air bubble that has a volume of 1 μL at 1 atmosphere will have an approximate volume of 0.2 μL at 50 psig (5 atm). As the bubble size shrinks, further casting solution fills the cavity further into the cavity and the area/volume ratio of the air bubble decreases allowing for a corresponding decrease in time required for the air to diffuse into the mold. While pressurization works well for a batch processes it is difficult and not economical to scale in order while maintaining high drug utilization. The leak pressure for a scaled batch process is an order of magnitude lower than the pressure necessary to effectively reduce air bubble size.

In a further approach described, for example, in U.S. Patent Publication No. 2008/0269685, a vacuum is applied to the mold after a casting solution is applied over the cavities in the mold. The vacuum causes the air bubbles in the cavities to expand and increase the force pushing the bubbles up through the casting solution. The air bubbles rise to the surface of the casting solution. Drying must be modulated to allow the air bubbles to rise completely through the casting solution or air voids will be formed within the microstructures as the solution dries.

Yet a further approach uses a soluble gas such as carbon dioxide ($CO_2$) to move the casting solution into or further into the cavities as described in U.S. Patent Publication No. 2014/0272101. The soluble gas displaces air in the cavities. Because the solubility and diffusivity of the soluble gas into the mold is significantly greater than air, the time required for any gas bubbles to permeate into the mold is reduced. While the high solubility and diffusivity of soluble gases such $CO_2$ are effective to reduce bubble size, some casting solution formulations are not compatible with the soluble gas. In particular, the soluble gas may adversely affect the pH or other characteristic of the casting solution and/or mold. For example, $CO_2$ gas may lower the pH of the casting solution, which presents the risk that the active agent may precipitate out of the solution. Thus, the effectiveness of using a soluble gas such as $CO_2$ may therefore be dependent upon the formulation of the casting solution. A further method of reducing, removing, or preventing air bubbles that is independent or relatively independent of the casting is therefore desirable.

In a preferred embodiment, a rough or low vacuum is applied to the mold prior to dispensing the casting solution on or in the mold to reduce the size of any air bubbles by removing the air in the cavities prior to dispensing the casting solution on or into the mold. Rather than applying a vacuum after the casting solution is dispensed onto or into the mold, the vacuum is applied prior to dispensing the casting solution to remove at least some of the air in the cavities prior to fill. In a preferred embodiment, a rough or low vacuum is applied to the mold prior to dispensing the casting solution. A rough or low vacuum is typically a vacuum that is slightly below atmospheric pressure. For convenience, the terms "rough vacuum", "low vacuum" and "medium" vacuum are used interchangeably hereafter. By "applied" with reference to a vacuum, it is typically intended that the mold is placed into and/or passed through a chamber or other container having the desired partial pressure. In embodiments, a low vacuum has a pressure of less than atmospheric (760 Torr). In embodiments, the low vacuum has a pressure range of less than about 760 to about 25 Torr.

In embodiments a vacuum of about 750-25, about 700-25, about 600-25, about 500-25, about 400-25, about 300-25, about 200-25, about 150-25, about 100-25, about 760-100, about 750-100, about 700-100, about 600-100, about 500-100, about 400-100, about 300-100, about 200-100, about 760-150, about 750-150, about 700-150, about 600-150, about 500-150, about 400-150, about 300-150, about 200-150, about 100-150, about 760-200, about 750-200, about 700-200, about 600-200, about 500-200, about 400-200, about 300-200, about 760-300, about 750-300, about 700-300, about 600-300, about 500-300, about 400-300, about 760-400, about 750-400, about 700-400, about 600-400, about 500-400, about 760-500, about 750-500, about 700-500, about 600-500, about 760-600, about 750-600, or about 700-600 Torr is applied to the mold prior to dispensing the casting solution.

Figure 3B:
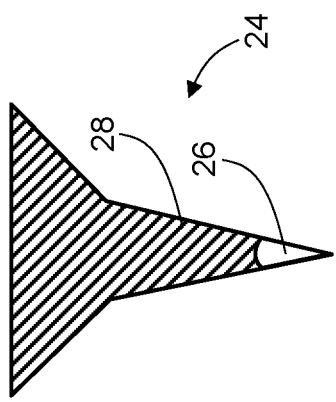
FIGS. 3A-3B are illustrations of molds containing solution without low vacuum (FIG. 3A) and with low vacuum (FIG. 3B).
Figure 3A:
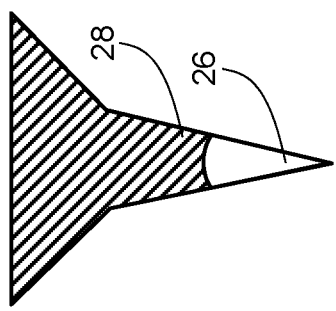

In embodiments, all or substantially all of the air in the cavities is removed by application of a low vacuum prior to dispensing the casting solution. The reduction in air in the cavities results in a corresponding decrease in the volume of air bubbles trapped between the casting solution and the mold as the cavities are filled. As shown in FIG. 3B, application of a 20% vacuum (0.15 atm) results in a volume of the air bubble 26 at the distal portion of the cavity of 0.15 μL. In comparison, when the casting solution 28 is cast at atmospheric pressure, the air bubble at the distal portion of the cavity 24 has a volume of 1 μL (FIG. 3A). In some embodiments, the cavities have an approximate volume of about 1-5 μL or more. Application of a low vacuum results in an 85% reduction in the volume of the air bubble as compared casting performed at atmospheric pressure. In embodiments, application of a low vacuum results in a 10-100% reduction in the volume of the distal air bubble as compared to the volume of an air bubble formed in the distal portion of the cavity at atmospheric pressure. In embodiments, application of a low vacuum results in a 10-90%, 10-80%, 10-70%, 10-60%, 10-50%, 10-40%, 10-30%, 10-20%, 20-100%, 20-90%, 20-80%, 20-70%, 20-60%, 20-50%, 20-40%, 20-30%, 30-100%, 30-90%, 30-80%, 30-70%, 30-60%, 30-50%, 30-40%, 40-100%, 40-90%, 40-80%, 40-70%, 40-60%, 40-50%, 50-100%, 50-90%, 50-80%, 50-70%, 50-60%, 60-100%, 60-90%, 60-80%, 60-70%, 70-100%, 70-90%, 70-80%, 80-100%, 80-90%, 90-100%, or 95-100% reduction in the volume of any distal air bubble as compared to the volume of an air bubble formed in the distal portion of the cavity at atmospheric pressure.

It will be appreciated that the step of applying a low vacuum prior to dispensing the casting solution may be combined with one or more known methods of reducing or eliminating air bubbles. In one example, the use of a soluble gas may be combined with application of low pressure to further reduce air bubbles. As seen in FIG. 1, a soluble gas such as $CO_2$ may be dispensed to the cavities to displace air in the cavities. A low vacuum is then applied to the mold to reduce the size of the soluble gas bubbles. A casting solution or formulation is dispensed onto the mold and/or into the mold cavities and dried. The embodiment as shown in FIG. 1 is a continuous or conveyer type system 10 where the mold comprising cavities 18 is moved through sections including the soluble gas (e.g. $CO_2$) dispensing section 12 (optional), the vacuum application section 14, and the formulation dispensing section 16, as shown. It will be appreciated that further sections including, but not limited to one or more drying sections 20 and further dispensing/vacuum sections may be included with the system. It will further be appreciated that the present methods may be performed sequentially but without the use of a continuous system.

After the low vacuum is applied, a casting solution or formulation 22 is dispensed onto the mold and/or into the mold cavities 18. It will be appreciated that the casting solution or formulation may be dispensed onto the mold and/or into the mold cavities while the low vacuum is applied. Where the solution is cast on the mold, the solution is moved into the cavities by any suitable means. In one embodiment, the mold surface with solution thereon is covered to spread the solution or formulation on the mold and at least partially into the cavities. In other embodiments, the solution is spread on the mold without covering. The cavities are filled with the casting solution.

In one embodiment, the mold is pressurized, with or without a cover, to move the solution into or further into the cavities of the mold. Pressurization may be accomplished by placing the mold with the casting solution into a pressure vessel as known in the art. Pressurization may involve a pressure of at least about 3 psi, about 5 psi, about 10 psi, about 14.7 psi, about 20 psi, or about 50 psi above atmospheric. In other embodiments, pressurization involves a pressure of at least about 3-50 psi above atmospheric. In other embodiments, pressurization involves a pressure of at least about 3-40 psi, about 3-30 psi, about 3-20 psi, about 3-14.7 psi, about 3-10 psi, about 3-5 psi, about 5-50 psi, about 5-30 psi, about 5-20 psi, about 5-14.7 psi, about 5-10 psi, about 10-50 psi, about 10-30 psi, about 10-20 psi, about 10-14.7 psi, about 20-50 psi, about 20-30 psi, or about 30-40 psi above atmospheric. Excess solution may be wiped or otherwise removed from the mold surface by any suitable means.

The mold with liquid casting solution is then dried using a single or multiple drying steps. Multiple and/or controlled drying steps are used to remove excess solvent and/or dry the microprojections. In one embodiment, the mold with liquid casting solution is dried at a temperature of about 5-50° C. for about 30 minutes to about 2 hours. It will be appreciated that the mold with liquid casting solution may be dried for any appropriate period of time to remove all or substantially all of the casting solution solvent(s). Drying may involve placing the mold with solution in an oven or other temperature controlled chamber. In another embodiment, a two-step primary drying method is used. The first step in a two-step drying method uses a slow drying method in which the mold with casting solution is dried under controlled humidity. Where the drying step involves controlling humidity, the mold is in dried in a chamber or section where humidity in the chamber is controlled from at least about 10% to about 95% relative humidity (RH). The mold with casting solution is initially dried for about 5 minutes to about an hour at a temperature of about 5-50° C. The second step involves drying without humidity control. In non-limiting embodiments, the second step involves drying the mold and casting solution/formulation at a temperature of about 5-50° C. for about 20-120 minutes or more. In another embodiment, the casting solution is dried in a chamber having a controlled partial pressure of the evaporate. Further, the mold with the liquid casting solution may be dried from beneath, under or below the mold. It will be appreciated that the casting solution may be dried from substantially beneath, under or below the mold. Specific embodiments of drying times, humidity, and/or drying conditions are disclosed in U.S. Patent Publication Nos. 2008/0269685 and 2014/0272101, which are incorporated herein by reference.

In one embodiment, an optional backing layer, base layer, or basement layer is further cast on the mold. A liquid backing formulation is dispensed on the mold or into the cavities. The liquid backing formulation is typically prepared by dissolving or suspending one or more polymers in a suitable solvent. In a preferred embodiment, the one or more polymers are biocompatible. Typically, but not always, the polymers are non-biodegradable. In another embodiment, the backing formulation may comprise one or more biodegradable and/or non-biodegradable polymers. Suitable biodegradable polymers are described above. Suitable non-biodegradable polymers are known in the art and include, but are not limited to, amphiphilic polyurethanes, polyether polyurethane (PEU), polyetheretherketone (PEEK), polylactic-co-glycolic acid) (PLGA), polylactic acid (PLA), polyethylene terephthalate, polycarbonate, acrylic polymers such as those sold under the trade name Eudragit®, polyvinylpyrrolidones (PVP), polyamide-imide (PAI), and/or co-polymers thereof. Further suitable polymers are described in U.S. Pat. No. 7,785,301, which is incorporated herein in its entirety. The backing formulation may include one or more excipients as described above for the active agent casting solution. In another embodiment, the backing layer is an adhesive layer. One suitable adhesive is the Dymax® 1187-M UV medical device adhesive. It will be appreciated that any biocompatible adhesive is suitable for use with, in and/or as the backing layer. This layer may also be a nonwoven or porous film double coated with pressure sensitive adhesive. Liquid backing formulations may be moved into the cavities by the same or similar methods as for the active agent casting solution.

Where a liquid backing layer formulation is used, the solvent of the backing layer formulation is removed by a drying process such that the resulting array has a backing layer with a plurality of microstructures extending at an angle from the backing layer. The drying conditions for drying the backing layer should be controlled so that the backing layer solvent can be removed effectively without affecting the stability of an active agent and/or to properly form (e.g. uniform) the backing layer. It will be appreciated that the conditions and methods for drying the active agent formulations as described above may be used for drying the backing layer formulations. In one embodiment, the mold is placed into a compressed dry air (CDA) box under controlled air flow and then placed in an oven at about 5-50° C. In further embodiments, the mold is placed in the oven at a temperature of about 5-50° C. In embodiments, the temperature of the CDA and/or oven is about 5° C., about 10° C., about 20° C., about 30° C., about 40° C., about 45° C., or about 50° C. In embodiments, the temperature of the CDA and/or oven is about 5-45° C., 5-40° C., 5-30° C., 5-20° C., 5-15° C., 5-10° C., 10-50° C., 10-45° C., 10-40° C., 10-30° C., 10-20° C., 10-15° C., 15-50° C., 15-45° C., 15-40° C., 15-30° C., 15-20° C., 20-50° C., 20-45° C., 20-40° C., 20-30° C., 30-50° C., 30-45° C., 30-40° C., 30-45° C., 40-50° C., 40-45° C., or 45-50° C. In embodiments, the oven uses convection, conduction, or radiation for drying. In another embodiment, the mold is placed in an oven at about 5-50° C. without prior time in a CDA box. In embodiments, the mold is placed in the CDA and/or oven for at least about 0-120 minutes, about 30-120 minutes, about 30-90 minutes, about 30-60 minutes, about 30-45 minutes, about 45-120 minutes, about 45-90 minutes, about 45-60 minutes, about 60-120 minutes, about 60-90 minutes, about 90-120 minutes, or longer. Residual solvents in the backing layer can be measured to determine the effectiveness of solvent removal under different drying conditions. The backing layer connects and/or supports the microprojection tips.

The backing layer with attached microstructures is demolded as described further below and undergoes an optional final drying step to form the microstructure array (MSA). Before or after the microprojection array is removed from the mold a final drying step may be performed. This final drying step may be performed under vacuum. The final drying may be at room temperature or at an elevated temperature. In embodiments, the final drying is at about 5-50° C. In embodiments, the final drying is at about 5° C., at about 10° C., at about 20° C., at about 25° C., at about 35° C., at about 40° C., at about 45° C., or at about 50° C. Further suitable temperatures and ranges are described above with reference to drying the backing layer. In embodiments, the final drying is from about 1-24 hours or longer, from about 4-20 hours, from about 6-10 hours, from about 8-16 hours, from about 8-12 hours, from about 8-10 hours, from about 10-12 hours, from about 10-16 hours, from about 12-16 hours or longer. In other embodiments, the final drying step is overnight. It will be appreciated that the MSA may be demolded prior to undergoing the final drying step.

Before or after the optional final drying step, the microprojection arrays may further and optionally be positioned on a base or substrate. The substrate may be in addition to or instead of a backing layer. The microprojections may be attached to the substrate by any suitable means. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax®. It will be appreciated that any medical device adhesive known in the art would be suitable. In one embodiment, the substrate is a breathable nonwoven pressure sensitive adhesive. The substrate is placed on the backing layer where present or a proximal surface of the microprojections. The substrate is adhered or attached to the microprojections. In another embodiment, the substrate is a UV cured adhesive in a polycarbonate film. The UV adhesive is dispensed on the top of the backing layer or the proximal surface of the microprojections, covered with a polycarbonate (PC) film to spread the adhesive and cured using a UV Fusion system. In one embodiment a UV curing dose is about 1.6 J/cm$^2$. After the substrate is attached or adhered to the microprojections, the microprojection array is removed from the mold. It will be appreciated where the array includes a backing layer the substrate is attached or adhered to the backing layer as described above for the microstructures.

Cast microprojection arrays are removed from the mold by any suitable means. In one embodiment, the microprojection array is removed from the mold by using a de-mold tool. A double-sided adhesive is placed on the back of microprojection array with one side for adhering to the array and the other side for adhering to the de-mold tool. The array is removed from the mold by gently rolling the de-mold tool over the adhesive on the back of the array with a slight rolling angle, such as about 1-90 degrees. The microprojection array is then gently peeled off from the de-mold tool. The arrays may be demolded after drying the backing layer or after a final drying step.

After the microprojection array is removed from the mold, it may be cut to an appropriate size and/or shape. In one embodiment, the microprojection array is die cut with an 11 or 16 mm punch.

II. MICROSTRUCTURE ARRAYS

General features of microstructure arrays suitable for use in the instant arrays and methods are described in detail in U.S. Patent Publication No. 2008/0269685, U.S. Patent Publication No. 2011/0006458, and U.S. Patent Publication No. 2011/0276028, the entire contents of which are explicitly incorporated herein by reference.

The microstructure arrays are preferably stable both during the fabrication process as described above and have a stable shelf life. Short-term stability of the arrays may be evaluated by storing the arrays at various temperatures and/or humidities and analyzing monomer content, composition purity, and deamidation of proteins by SEC-HPLC, RP-HPLC, and IEX-HPLC. The liquid casting solution or formulation is preferably stable during the fabrication process, which typically lasts a few hours. Preferably, the liquid casting solution is stable for a period of 30 minutes to 6 hours. In non-limiting embodiments, the liquid casting solution is stable for a period of at least from 30 minutes to 1 hour, from 30 minutes to 2 hours, from 30 minutes to 3 hours, from 30 minutes to 4 hours, from 30 minutes to 5 hours, from 1-6 hours, from 1-5 hours, from 1-4 hours, from 1-3 hours, from 1-2 hours, from 2-6 hours, from 2-5 hours, from 2-4 hours, from 2-3 hours, from 3-6 hours, from 3-5 hours, from 3-4 hours, from 4-6 hours, from 4-5 hours, or from 5-6 hours. In specific, but not limiting embodiments, the liquid casting solution is stable for at least about 30 minutes, about 45 minutes, about 1 hour, about 2 hours, about 3 hours, about 4 hours, about 5 hours, about 6 hours, or longer. The microstructure arrays are preferably stable for at least about one day when stored at about room temperature (e.g. about 25° C.). In other embodiments, the arrays are preferably stable for at least about 1 week when stored at about 5° C. In other embodiments, the arrays are stable when stored at an elevated temperature (e.g. about 40° C.) for at least about 1-12 weeks, about 1-16 weeks, or about 1-32 weeks. In other embodiments, the arrays are stable when stored at about 5° C. for at least about 1-52 weeks or 1-156 weeks. It will be appreciated that the shelf-life may vary depending on the storage temperature. In embodiments, the arrays are stable when stored at about 5° C. for at least about 1-156 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In embodiments, the arrays are stable when stored at about 40° C. for at least about 1-26 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In other embodiments, the arrays are stable when stored at about 25° C. for at least about 1-14 days. In further embodiments, the arrays are stable when stored at about 25° C. for at least about 1-12 weeks, about 1-16 weeks, about 1-104 weeks, or about 1-156 weeks. In specific, but not limiting embodiments, the arrays are stable when stored at about 5° C. for at least about 5 days, at least about 1 week, at least about 2 weeks, at least about 4 weeks, at least about 5 weeks, at least about 6 weeks, or longer. In embodiments, the arrays are stable when stored at about 25° C. for at least about 1-2 days, about 1-5 days, about 1-7 days, about 1-10 days, about 2-5 days, about 2-7 days, about 2-10 days, about 2-14 days, about 3-5 days, about 3-7 days, about 3-10 days, about 3-14 days, about 5-14 days, about 5-10 days, about 5-14 days, or about 10-14 days. In specific, but not limiting, embodiments, the arrays are stable when stored at about 25° C. for at least about 12 hours, at least about 1 day, at least about 2 days, at least about 3 days, at least about 4 days, at least about 5 days, at least about 6 days, at least about one week, or longer. Stability is typically monitored by measuring the purity of the active agent in the array after storage as compared to an array before storage (time=0). In embodiments, the array has a purity of at least about 80-100%, about 85-100%, about 90-100%, about 95-100%, about 80-95%, about 85-95%, about 90-95% about 80-90%, about 85-90% or about 80-85% after storage. In non-limiting embodiments, the array has a purity of at least about 80%, about 85%, about 90%, about 92%, about 93%, about 95%, about 96%, about 97%, about 98%, about 99%, or about 100% after storage.

Where the active agent is a protein, Methionine-oxidation (Met-oxidation) is preferably less than or equal to 1-20% after storage for about 1-6 weeks at about 5° C.-40° C. In embodiments Met-oxidation is less than about 1-10%, about 1-5%, about 1-6%, about 2-3%, about 2-4%, about 2-5%, 2-6%, about 3-5%, or about 3-6%. In specific, but not limiting, embodiments, Met-oxidation is less than about 1%, about 2%, about 3%, about 4%, about 5%, about 6%, or about 10%.

The microstructure arrays should have sufficient mechanical strength to at least partially penetrate the stratum corneum or other membrane surface of a subject. It will be appreciated that different mechanical strength will be required for application at different sites. One method for assessing mechanical strength is a skin-penetration efficiency (SPE) study as described U.S. Patent Publication No. 2014/0272101. Preferably, the arrays have a SPE of at least about 50-100%. In other embodiments, the arrays have a SPE of at least about 50-80%, about 50-85%, about 50-90%, about 50-95%, about 60-80%, about 60-85%, about 60-90%, about 60-95%, about 60-100%, about 75-80%, about 75-85%, about 75-90%, about 75-95%, about 75-100%, about 80-85%, about 80-90%, about 80-95%, about 80-100%, about 90-95%, and about 90-100%. In specific, non-limiting, embodiments, the arrays have a SPE of at least about 50%, 60%, 70%, 75%, 80%, 85%, 90%, 95%, 99%, and 100%.

Preferably, at least about 50-100% of the active agent is delivered by the MSAs described herein. Delivery efficiency may be determined by preparing the MSA and applying the MSA in vivo or in vitro. In embodiments, the MSA has a delivery efficiency of at least about 50-60%, about 50-70%, about 50-75%, about 50-80%, about 50-90%, about 50-95%, about 50-99%, about 60-70%, about 60-75%, about 60-80%, about 60-90%, about 60-95%, about 60-99%, about 70-75%, about 70-80%, about 70-90%, about 70-95%, about 70-99%, about 75-80%, about 75-90%, about 75-95%, about 75-99%, about 80-90%, about 80-95%, about 80-99%, about 90-95%, about 90-99%, or about 95-99%.

III. METHODS OF USE

The methods, kits, microstructure arrays and related devices described herein may be used for treating any condition. It will be appreciated that the microstructure arrays may be used with any appropriate applicator including the applicator described in U.S. Publication No. 2011/0276027, as well as those described in U.S. Publication No. 2014/0276580 and 2014/0276366, each of which are incorporated herein in their entirety.

IV. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Preparing Microstructure Arrays

A silicone mold comprising a plurality of microstructure cavities is purged with carbon dioxide ($CO_2$). The mold is placed in a vacuum of less than 1 atm. About 90 µL of a liquid formulation comprising an active agent is dispensed onto the mold from a reservoir using a syringe or fountain type reservoir. The mold containing the formulation is pressurized for 1 minute at about 50 psi. The mold surface is then wiped to remove excess formulation from the mold surface.

Depending on the physiochemical properties of the liquid formulation (viscosity, solid content, surface interaction between formulation and mold, etc.), the formulation is dried using either one or two primary drying steps. The one step primary drying comprises directly placing the mold comprising the liquid formulation in an incubator oven at 32° C. for about 30 minutes to remove solvents.

In the two step primary drying, a slow drying step is followed by a second drying step. The mold with the liquid formulation is placed in a chamber where the humidity is controlled to about 50% to 90% relative humidity (RH), at room temperature for about 5 to 30 minutes. The air convection in the chamber may also be controlled. The mold with formulation is then incubated for about 30 minutes in an oven at about 30° C. to 35° C.

A backing layer liquid formulation is then dispensed onto the mold surface from a second reservoir. The backing layer formulation is moved into the mold cavities to contact the dried active agent formulation. The backing layer formulation dried to remove the solvent. The mold with the backing layer formulation is placed into a compressed dry air box for about 30 minutes with controlled air flow, and then placed in a convection oven at about 40° C. to 50° C. for about 90 minutes. The backing layer formulation contacts the drug formulation to connect and support the drug formulation, which becomes the distal tip or portion of the microstructures.

A breathable, nonwoven pressure sensitive adhesive is placed on the dried backing layer to form a substrate layer. Alternatively, a UV adhesive is dispensed on the top of the backing layer, covered with 5 ml polycarbonate (PC) film to spread the adhesive, and then cured using a UV Fusion system. The UV curing dose is about 1.6 $J/cm^2$.

The microstructure array comprising the drug-in-tip (DIT) layer comprising the active agent, the backing layer and the substrate is demolded or removed from the mold. The array is die cut with an 11 mm or 16 mm punch. The microstructure array is dried under vacuum (~0.05 torr) at room temperature (~35° C.) overnight.

Embodiments

1. A method of making an array of microstructures comprising:
   (a) dissolving or suspending at least one therapeutic agent in a first solvent to form a therapeutic agent solution or suspension;
   (b) dissolving at least one polymer in a second solvent to form a polymer matrix solution or suspension;
   (c) mixing the therapeutic agent solution or suspension and the polymer solution or suspension to form a polymer matrix solution or suspension;
   (d) applying a low vacuum to a mold having an array of microstructure cavities;
   (e) dispensing the polymer matrix solution or suspension on the mold;
   (f) filling the microstructure cavities in the mold;
   (g) drying the solution or suspension to form the array of microstructures.
2. The method of embodiment 1, wherein the low vacuum is applied to achieve a vacuum pressure of about $1 \times 10^{-3}$ to 760 Torr.
3. The method of the combined or separate embodiments 1-2, wherein the low vacuum is applied to achieve a vacuum pressure of about 25 to 760 Torr.
4. The method of the combined or separate embodiments 1-3, wherein step (f) is performed outside of the low vacuum.
5. The method of the combined or separate embodiments 1-4, further comprising:
   after step (f), removing excess polymer matrix solution or suspension on the mold surface.
6. The method of the combined or separate embodiments 1-5, wherein the polymer matrix solution or suspension is dried at a temperature of about 5-50° C.
7. The method of the combined or separate embodiments 1-6, wherein the polymer matrix solution or suspension is dried for at least about 30-60 minutes.
8. The method of the combined or separate embodiments 1-7, further comprising:
   dispensing a basement or backing layer formulation on the mold surface; and drying the basement or backing layer formulation.
9. The method of the combined or separate embodiments 1-8, wherein the basement or backing layer is comprised of at least one non-biodegradable polymer.
10. The method of the combined or separate embodiments 1-9, wherein drying the basement or backing layer comprising drying in an oven at about 5-50° C.
11. The method of the combined or separate embodiments 1-10, further comprising:
    affixing the basement or backing layer to a substrate.
12. The method of the combined or separate embodiments 1-11, wherein the substrate is selected from a pressure sensitive adhesive and a UV cured adhesive.
13. The method of the combined or separate embodiments 1-12, further comprising dispensing at least one soluble gas into the cavities prior to applying the low vacuum to the mold.
14. The method of the combined or separate embodiments 1-13, further comprising dispensing at least one soluble gas into the cavities prior to dispensing the polymer matrix solution or suspension on the mold.

15. The method of the combined or separate embodiments 1-14, wherein the soluble gas is selected from $CO_2$ and $CH_4$.

16. The method of the combined or separate embodiments 1-15, wherein at least one of the first or second solvent is water or an aqueous solution.

17. The method of the combined or separate embodiments 1-16, further comprising:
demolding the microstructure array.

18. The method of the combined or separate embodiments 1-17, further comprising:
demolding the microstructure array after drying the basement or backing layer.

19. The method of the combined or separate embodiments 1-18, further comprising:
dissolving at least one of a sugar, a surfactant, or an antioxidant in at least one of the first or the second solvent.

20. The method of the combined or separate embodiments 1-19, wherein the sugar is selected from sorbitol, sucrose, trehalose, fructose, or dextrose.

21. The method of the combined or separate embodiments 1-20, wherein the surfactant is selected from Polysorbate 20 or Polysorbate 80.

22. The method of the combined or separate embodiments 1-21, wherein the antioxidant is selected from methionine, cysteine, D-alpha tocopherol acetate, EDTA, or vitamin E.

23. The method of the combined or separate embodiments 1-22, further comprising:
dissolving a sugar in the polymer matrix solution or suspension after step (b).

24. The method of the combined or separate embodiments 1-23, wherein the therapeutic agent is selected from a drug, a small molecule, a peptide or protein, or a vaccine.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A method of making an array of microstructures employing a continuous conveyor system, said system comprising a movable mold having an array of microstructure cavities, a soluble gas dispensing section, a vacuum application section, a formulation dispensing section and a drying section, the method comprising:
   (a) dissolving or suspending at least one therapeutic agent in a first solvent to form a therapeutic agent solution or therapeutic agent suspension;
   (b) dissolving at least one polymer in a second solvent to form a polymer solution or polymer suspension;
   (c) mixing
      (i) the therapeutic agent solution or therapeutic agent suspension and
      (ii) the polymer solution or polymer suspension to form a casting solution or casting formulation;
   (d) exposing the movable mold having an array of microstructure cavities to at least one of carbon dioxide ($CO_2$) gas or methane ($CH_4$) gas in the soluble gas dispensing section, where solubility and diffusivity of the $CO_2$ gas or $CH_4$ gas is greater in the mold compared to solubility and diffusivity of the $CO_2$ gas or $CH_4$ gas in air;
   (e) applying a low vacuum to the movable mold having an array of microstructure cavities in the vacuum application section, wherein at least 90% of air in the cavities is removed by application of the low vacuum prior to dispensing the casting solution or casting formulation;
   (f) dispensing the casting solution or casting formulation onto the mold in the formulation dispensing section;
   (g) filling the microstructure cavities in the mold with the casting solution or casting formulation; and
   (h) drying the casting solution or casting formulation to form the array of microstructures in the drying section.

2. The method of claim 1, wherein the low vacuum is applied to achieve a vacuum pressure of about $1 \times 10^{-3}$ to less than about 760 Torr.

3. The method of claim 1, wherein the low vacuum is applied to achieve a vacuum pressure of about 25 to less than about 760 Torr.

4. The method of claim 1, further comprising:
after step (g), removing excess casting solution or casting formulation on the mold surface.

5. The method of claim 1, wherein the drying of step (h) comprises drying at a temperature of about 5-50° C.

6. The method of claim 1, wherein the drying of step (h) comprises drying for at least about 30-60 minutes.

7. The method of claim 1, further comprising after step (h):
dispensing a basement or backing layer formulation on the mold surface; and
drying the basement or backing layer formulation, thereby forming a basement or backing layer on the array of microstructures.

8. The method of claim 7, wherein the basement or backing layer is comprised of at least one non-biodegradable polymer.

9. The method of claim 7, wherein drying the basement or backing layer formulation comprises drying at about 5-50° C.

10. The method of claim 7, further comprising:
affixing the basement or backing layer to a substrate.

11. The method of claim 10, wherein the substrate is selected from a pressure sensitive adhesive and a UV cured adhesive.

12. The method of claim 1, wherein at least one of the first or second solvent is water or an aqueous solution.

13. The method of claim 1, further comprising after step (h):
demolding the microstructure array.

14. The method of claim 7, further comprising:
demolding the microstructure array after drying the basement or backing layer formulation.

15. The method of claim 1, further comprising:
dissolving at least one of a sugar, a surfactant, or an antioxidant in at least one of the first or the second solvent prior to step (c).

16. The method of claim 15, wherein the sugar is selected from sorbitol, sucrose, trehalose, fructose, or dextrose.

17. The method of claim 15, wherein the surfactant is selected from polyoxyethylene (20) sorbitan monolaurate or polyoxyethylene (20) sorbitan monooleate.

18. The method of claim 15, wherein the antioxidant is selected from methionine, cysteine, D-alpha tocopherol acetate, EDTA, or vitamin E.

19. The method of claim 1, further comprising:
dissolving a sugar in the casting solution or casting formulation prior to step (f).

20. The method of claim 1, wherein the therapeutic agent is selected from a drug, a small molecule, a peptide or protein, or a vaccine.

21. The method of claim 1, wherein the microstructure cavities in the movable mold comprising the casting solution or casting formulation are pressurized for a period of time between steps (g) and (h).

22. A method for making an array of microstructures employing a continuous conveyor system, said system comprising a movable mold having an array of microstructure cavities, a soluble gas dispensing section, a vacuum application section, a formulation dispensing section and a drying section, the method comprising:
(a) providing a casting formulation, said formulation comprising:
  (i) a solvent or combination of solvents,
  (ii) at least one polymer dissolved in said solvent or combination of solvents, and
  (iii) at least one therapeutic agent dissolved or suspended in said solvent or combination of solvents;
(b) exposing the movable mold having an array of microstructure cavities to at least one of carbon dioxide ($CO_2$) gas or methane ($CH_4$) gas in the soluble gas dispensing section, where solubility and diffusivity of the $CO_2$ gas or $CH_4$ gas is greater in the mold compared to solubility and diffusivity of the $CO_2$ gas or $CH_4$ gas in air;
(c) applying a low vacuum to the movable mold having an array of microstructure cavities in the vacuum application section, thereby removing at least 90% of the air from the microstructure cavities;
(d) dispensing the casting formulation onto the mold in the formulation dispensing section;
(e) filling the microstructure cavities in the mold with the casting formulation; and
(f) drying the casting formulation to form the array of microstructures in the drying section.

23. The method of claim 21, wherein the microstructure cavities in the movable mold comprising the casting solution or casting formulation are pressurized for a period of time between steps (e) and (f).

* * * * *